(12) United States Patent
Walz et al.

(10) Patent No.: US 8,026,295 B2
(45) Date of Patent: Sep. 27, 2011

(54) DENTAL COMPOSITION WITH IMPROVED LIGHT STABILITY

(75) Inventors: Uwe Walz, Konstanz (DE); Joachim E. Klee, Radolfzell (DE)

(73) Assignee: Dentsply International, Inc., York, PA (US)

(*) Notice: Subject to any disclaimer, the term of this patent is extended or adjusted under 35 U.S.C. 154(b) by 34 days.

(21) Appl. No.: 12/002,550

(22) Filed: Dec. 18, 2007

(65) Prior Publication Data
US 2008/0103229 A1    May 1, 2008

Related U.S. Application Data

(63) Continuation-in-part of application No. 10/452,739, filed on Jun. 2, 2003, now abandoned, which is a continuation of application No. 09/754,162, filed on Jan. 4, 2001, now abandoned.

(60) Provisional application No. 60/183,269, filed on Feb. 17, 2000.

(51) Int. Cl.
*A61K 6/083* (2006.01)
*C08K 5/34* (2006.01)

(52) U.S. Cl. .......... 523/115; 523/116; 524/89; 524/102; 433/228.1

(58) Field of Classification Search .................. 523/115, 523/116; 524/89, 102
See application file for complete search history.

(56) References Cited

U.S. PATENT DOCUMENTS

| | | | |
|---|---|---|---|
| 4,182,829 A | 1/1980 | Walkowiak et al. | |
| 4,297,266 A | 10/1981 | Ibsen et al. | |
| 4,323,348 A | 4/1982 | Schmitz-Josten et al. | |
| 4,457,818 A | 7/1984 | Denyer et al. | |
| 4,525,256 A | 6/1985 | Martin | |
| 4,558,120 A | 12/1985 | Tomalia et al. | |
| 4,587,329 A | 5/1986 | Tomalia et al. | |
| 4,746,686 A | 5/1988 | Waller | |
| 4,857,599 A | 8/1989 | Tomalia et al. | |
| 4,952,241 A | 8/1990 | Reiners et al. | |
| 5,274,064 A | 12/1993 | Sarkar | |
| 5,308,886 A | 5/1994 | Masuhara et al. | |
| 5,395,883 A | 3/1995 | Yates, III et al. | |
| 5,418,301 A | 5/1995 | Hult et al. | |
| 5,468,789 A | 11/1995 | Lewis et al. | |
| 5,486,548 A | 1/1996 | Podszun et al. | |
| 5,530,092 A | 6/1996 | Meijer et al. | |
| 5,679,794 A | 10/1997 | Suhadolnik et al. | |
| 5,814,681 A | 9/1998 | Hino et al. | |
| 5,914,379 A | 6/1999 | Sutoris et al. | |
| 5,985,958 A | 11/1999 | Moszner et al. | |
| 6,025,114 A | 2/2000 | Popat et al. | |
| 6,030,606 A | 2/2000 | Holmes | |
| 6,121,344 A | 9/2000 | Angeletakis et al. | |
| 6,300,533 B1 | 10/2001 | Benage et al. | |
| 6,552,130 B1 * | 4/2003 | Makino et al. | 525/222 |

FOREIGN PATENT DOCUMENTS

| | | |
|---|---|---|
| DE | 2724260 | 12/1978 |
| EP | 0716103 | 6/1996 |
| EP | 0995421 | 4/2000 |
| EP | 0765856 | 10/2003 |
| EP | 1255524 | 12/2005 |
| EP | 1563821 | 11/2006 |
| GB | 1218456 | 9/1968 |
| SU | 334845 | 1/1984 |
| WO | WO 97/02328 | 1/1997 |
| WO | WO 97/47272 | 12/1997 |
| WO | WO 01/60322 | 8/2001 |

OTHER PUBLICATIONS

Standish et al, "Cure of resin based restorative materials. I. Self cure resins", Australian Dental Journal, Apr. 1983, pp. 82-86, vol. 28, No. 2.
Cook et al. "Cure of resin based restorative materials. II. White light photopolymerized resins", Australian Dental Journal, Oct. 1983, pp. 307-311, vol. 28, No. 5.
Cook et al, "Polymerization kinetics of resin-based restorative materials," Journal of Biomedical Materials Research, 1983, pp. 275-282, vol. 17.
Liso et al. "Analysis of the leaching and toxicity of new amine activators for the curing of acrylic bone cenents and composites", Biomaterials 1997, pp. 15-20, vol. 18, No. 1.
Diplock et al, "Functional food science and defence against reactive oxidative species", NCBI National Library of Medicine,Br J Nutr Aug. 1998;80 Suppl 1:S77-112, 2 pgs.
Thompsn, "Antioxidants and hormone-mediated health benefits of whole grains", NCBI National Library of Medicine, Crit Rev Food Sci Nutr 1994;34(5-6):473-97, 1 pg.
Santerre, "Effect of filler content on the profile of released biodegradation porducts in micro-filled bis-GMA/TEGDMA dental composite resins", NCBI Nat'l Library of Medicine 1999.
Gerzia, "Bioavailability of components of resin-based materials which are applied to teeth", NCBI National Library of Medicine, Crit Rev Oral Biol Med 1996;7(2):172-9, 1 pg.

* cited by examiner

*Primary Examiner* — Tae H Yoon
(74) *Attorney, Agent, or Firm* — Douglas J. Hura; Leana Levin; David A. Zdurne

(57) ABSTRACT

Dental composition having an improved light and thermal stability, including a mixture of at least a polymerizable resin, at least a polymerizable monomer, at least a polymerization initiator and/or a sensitizer and stabilizer, and at least an organic and/or inorganic filler and pigments in a content of 0 to 90 percent and at least one of the stable radicals.

10 Claims, No Drawings

DENTAL COMPOSITION WITH IMPROVED LIGHT STABILITY

RELATED APPLICATIONS

This is a continuation-in-part application of U.S. patent application Ser. No. 10/452,739 filed on Jun. 2, 2003 (abandoned); which is a continuation application of U.S. patent application Ser. No. 09/754,162 filed on Jan. 4, 2001 (abandoned); which was filed off of U.S. provisional patent application Ser. No. 60/183,269 filed on Feb. 17, 2000.

Claimed is a light curing dental composition with improved light sensitivity comprising prepolymers, macromonomers or polymers having at least one N-1-oxyl moiety, preferably a 4-Amino-2,2,6,6-tetramethylpiperidin-1 oxyl moiety.

TECHNICAL BACKGROUND

Dental compositions comprise polymerizable acrylates and/or methacrylates that are stabilized against spontaneous polymerization by using of free-radical scavenger such as the well-known phenols 2,6-di-tert.-butyl-4-cresol (BHT), hydroquinone or hydroquinone monomethylether (HQME). On the other side they contains a photoinitiator that must be react sensible to visible or UV-light to photoinitiate the free-radical polymerization.

Light curing dental materials mostly are applied under the conditions of relatively strong operating lamps. Consequently, the international standards require that a dental composite remains stable under an illumination of 10,000 lux for 60 seconds (ISO 4049), that a dental pit and fissure sealant and a light activated water based cement remains stable under an illumination of 8,000 lux for 25 seconds (ISO 6874) and for 30 s (ISO 9917-2), respectively.

To improve light stability an optimization of the initiator/inhibitor system leads to lengthening the working times under the conditions of a dental practice. However, this optimization is limited and leads to minor reduction of light sensitivity only.

Recently, it was found, that stable organic radicals reduce the light sensitivity of a dental light-curing composite material (N. Moszner, V. Rheinberger, U.S. Pat. No. 5,847,025) when low molecular stable radicals such as 2,2-Diphenyl-1-picrylhydrazyl radicals, galvinoxyl radicals and/or triphenylmethyl radicals or 2,2,6,6-tetramethylpiperidin-1oxyl radicals are applied.

In the last decades dental composites becomes popularly as consequence of an improved dental supply. However, the application of this material class is combined with some new risks due to the release of parts of the composite, namely partly non-polymerized monomers (L. Shajii, J. P. Santerre, Biomaterials 20 (1999) 1897, W. R. Hume, T. M. Gerzia, Crit. Rev. Oral. Biol. Med. 7 (1996) 172) as well as portions of the inhibitors and/or initiator system (P. A. Liso et al., Biomaterials 18 (1997) 15). Furthermore, it is well known that free-radicals bearing some health risk (A. T. Diplock et al., Br. J. Nutr. 80 (1998), Suppl 1, 77; L. U. Thompson, Crit. Rev. Food Sci. Nutr. 34 (1994), 473).

Consequently, it seems desirable to use stable free-radicals for improved light sensitivity and to link them into the polymer system in order to avoid penetration and health risks.

The low molecular stable radicals that are suggested in U.S. Pat. No. 5,847,025 bases on piperidinium 1-oxyl radicals bearing phenol or thiophenol groups or derivatives of carboxylic or thiocarboxylic acids.

DESCRIPTION OF THE INVENTION

Invented was a dental composition having an improved light and thermal stability, comprising a mixture of (i) at least a polymerizable resin (ii) at least a polymerizable monomer (iii) at least a polymerization initiator and/or a sensitizer and stabilizer (iv) at least an organic and/or inorganic filler and pigments in a content of 0 to 90 percent (v) and at least one of the stable radicals of formulas 1 to 5

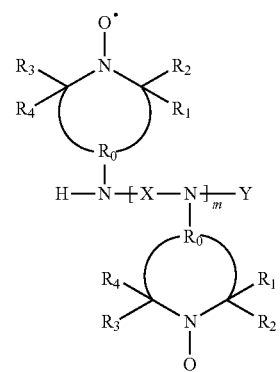

1

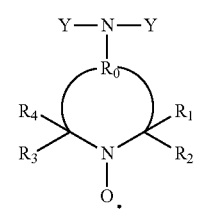

2

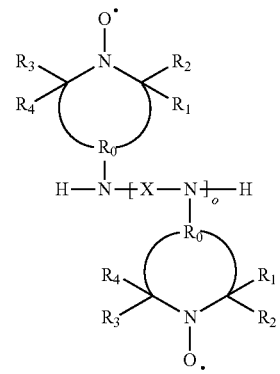

3

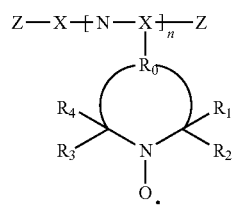

4

-continued

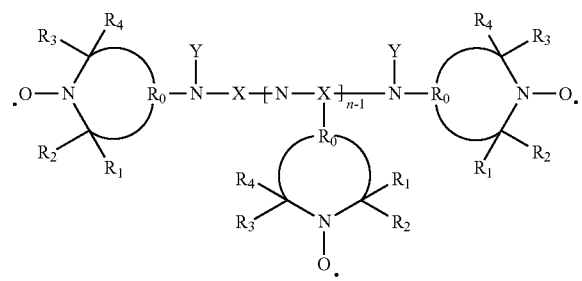

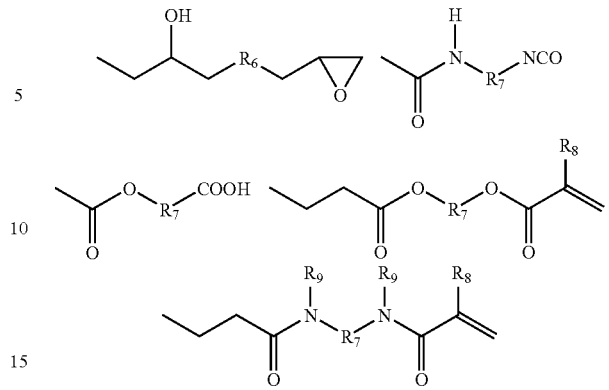

wherein $R_0$ denotes a substituted or unsubstituted $C_1$ to $C_{18}$ alkylene, $R_1, R_2, R_3$ and $R_4$ denotes a substituted or unsubstituted $C_1$ to $C_{18}$ alkylene, preferably a methyl group X denotes a difunctional substituted or unsubstituted $C_2$ to $C_{30}$ alkylene, $C_5$ to $C_{30}$ substituted or unsubstituted cycloalkylene, substituted or unsubstituted $C_5$ to $C_{30}$ arylene or heteroarylene, preferably the following structures

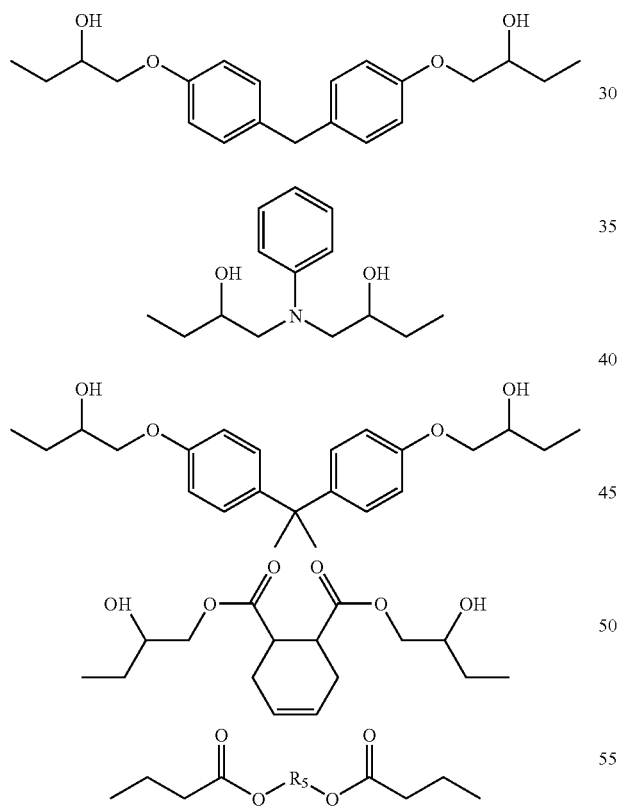

wherein $R_5$ denotes a difunctional substituted or unsubstituted $C_1$ to $C_{18}$ alkylene, $C_5$ to $C_{18}$ substituted or unsubstituted cycloalkylene, substituted or unsubstituted $C_5$ to $C_{18}$ arylene or heteroarylene, Y denotes H or a monofunctional substituted or unsubstituted $C_1$ to $C_{18}$ alkyl, $C_5$ to $C_{18}$ substituted or unsubstituted cycloalkyl, substituted or unsubstituted $C_5$ to $C_{18}$ aryl or heteroaryl, preferably selected from the group wherein $R_6$ denotes a difunctional substituted or unsubstituted $C_1$ to $C_{18}$ alkylene, $C_5$ to $C_{18}$ substituted or unsubstituted cycloalkylene, substituted or unsubstituted $C_5$ to $C_{18}$ arylene or heteroarylene, preferably

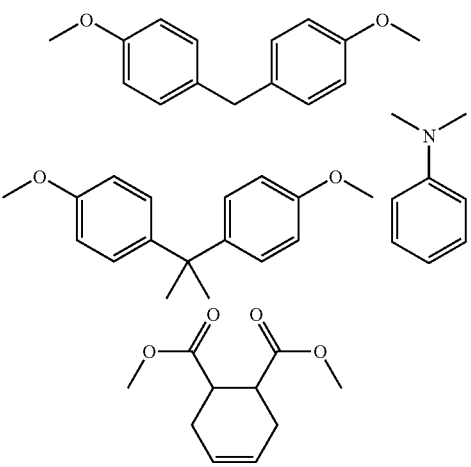

$R_7$ denotes difunctional substituted or unsubstituted $C_1$ to $C_{18}$ alkylene, $C_5$ to $C_{18}$ substituted or unsubstituted cycloalkylene, substituted or unsubstituted $C_5$ to $C_{18}$ arylene or heteroarylene, preferably selected from the group $R_8$ denotes H or a monofunctional substituted or unsubstituted $C_1$ to $C_{30}$ alkylene, $C_5$ to $C_{30}$ substituted or unsubstituted cycloalkylene, substituted or unsubstituted $C_5$ to $C_{30}$ arylene or heteroarylene $R_9$ denotes a monofunctional substituted or unsubstituted $C_1$ to $C_{30}$ alkylene, $C_5$ to $C_{30}$ substituted or unsubstituted cycloalkylene, substituted or unsubstituted $C_5$ to $C_{30}$ arylene or heteroarylene Z denotes hydrogen, or a polymerizable moiety, preferably selected from the group of

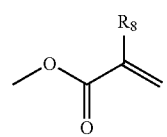

wherein $R_8$ denotes H or a monofunctional substituted or unsubstituted $C_1$ to $C_{30}$ alkylene, $C_5$ to $C_{30}$ substituted or unsubstituted cycloalkylene, substituted or unsubstituted $C_5$ to $C_{30}$ arylene or heteroarylene n, m and o are integers.

Preferably the dental composition comprises at least one of the compounds 6 to 10 which having at least one piperidinium nitroxyl radical moiety 6
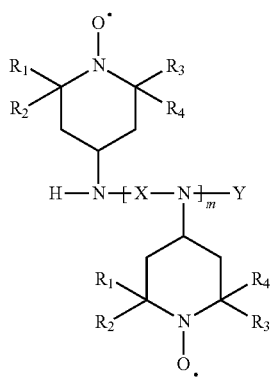

7
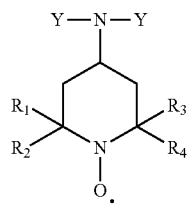

8
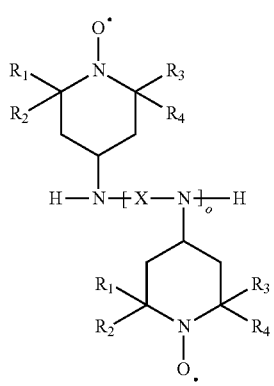

9
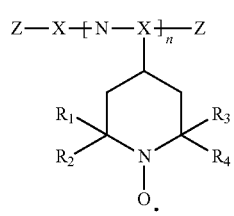

10
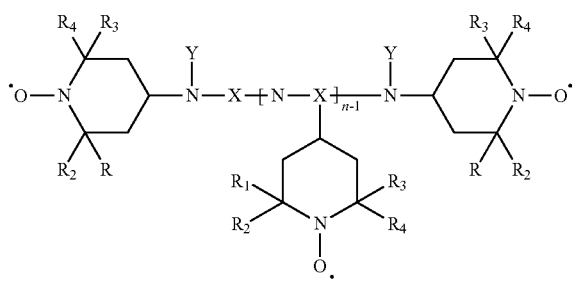

wherein $R_1$, $R_2$, $R_3$ and $R_4$ denotes a substituted or unsubstituted $C_1$ to $C_{18}$ alkylene, preferably methyl group X denotes a difunctional substituted or unsubstituted $C_2$ to $C_{30}$ alkylene, $C_5$ to $C_{30}$ substituted or unsubstituted cycloalkylene, substituted or unsubstituted $C_5$ to $C_{30}$ arylene or heteroarylene, preferably the following structures

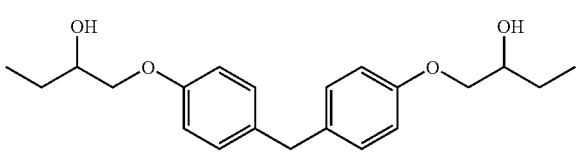

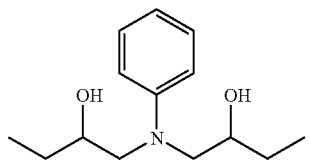

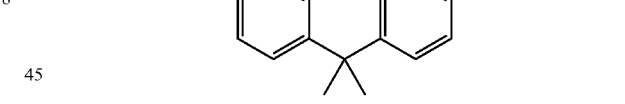

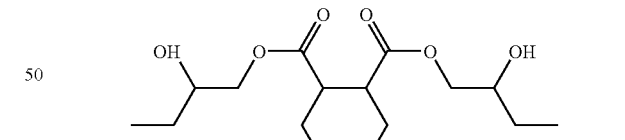

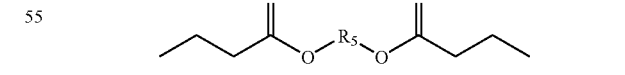

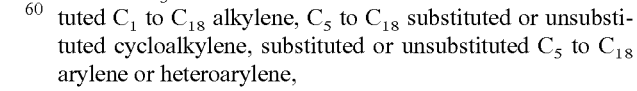

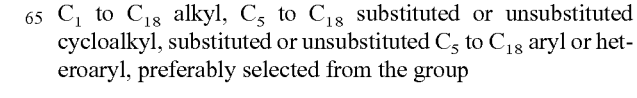

wherein $R_5$ denotes a difunctional substituted or unsubstituted $C_1$ to $C_{18}$ alkylene, $C_5$ to $C_{18}$ substituted or unsubstituted cycloalkylene, substituted or unsubstituted $C_5$ to $C_{18}$ arylene or heteroarylene, Y denotes H or a monofunctional substituted or unsubstituted $C_1$ to $C_{18}$ alkyl, $C_5$ to $C_{18}$ substituted or unsubstituted cycloalkyl, substituted or unsubstituted $C_5$ to $C_{18}$ aryl or heteroaryl, preferably selected from the group

7

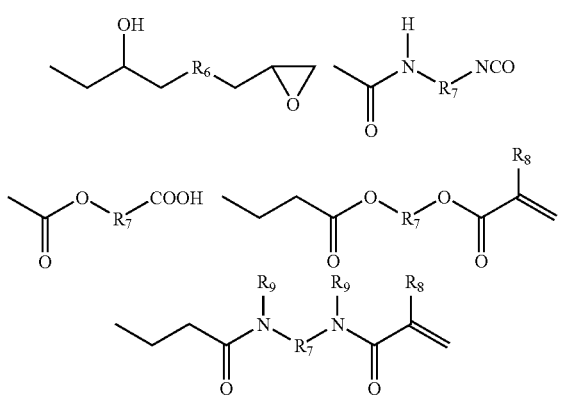

wherein $R_6$ denotes a difunctional substituted or unsubstituted $C_1$ to $C_{18}$ alkylene, $C_5$ to $C_{18}$ substituted or unsubstituted cycloalkylene, substituted or unsubstituted $C_5$ to $C_{18}$ arylene or heteroarylene, preferably

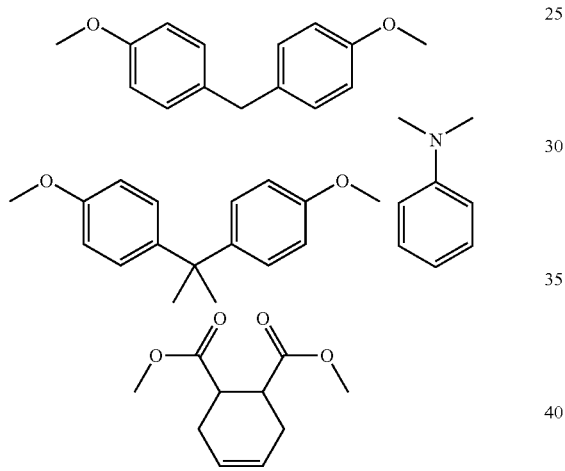

$R_7$ denotes difunctional substituted or unsubstituted $C_1$ to $C_{18}$ alkylene, $C_5$ to $C_{18}$ substituted or unsubstituted cycloalkylene, substituted or unsubstituted $C_5$ to $C_{18}$ arylene or heteroarylene, preferably selected from the group $R_8$ denotes H or a monofunctional substituted or unsubstituted $C_1$ to $C_{30}$ alkylene, $C_5$ to $C_{30}$ substituted or unsubstituted cycloalkylene, substituted or unsubstituted $C_5$ to $C_{30}$ arylene or heteroarylene $R_9$ denotes a monofunctional substituted or unsubstituted $C_1$ to $C_{30}$ alkylene, $C_5$ to $C_{30}$ substituted or unsubstituted cycloalkylene, substituted or unsubstituted $C_5$ to $C_{30}$ arylene or heteroarylene Z denotes hydrogen, or a polymerizable moiety, preferably selected from the group of

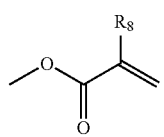

8 wherein $R_8$ denotes H or a monofunctional substituted or unsubstituted $C_1$ to $C_{30}$ alkylene, $C_5$ to $C_{30}$ substituted or unsubstituted cycloalkylene, substituted or unsubstituted $C_5$ to $C_{30}$ arylene or heteroarylene n, m and o are integers.

The piperidinium nitroxyl radical moieties were obtained by two different pathways, namely by oxidation of the following compounds 11 to 15 or by incorporation of an amine comprising at least a nitroxyl radical moieties.

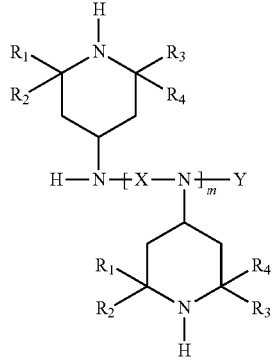

11

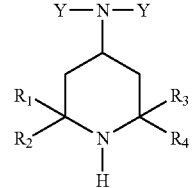

12

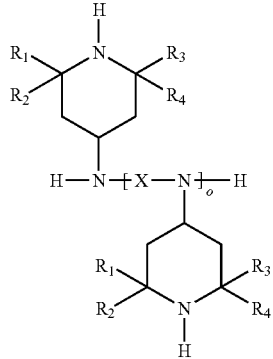

13

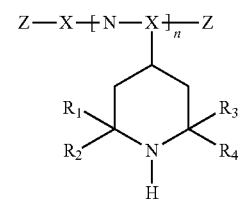

14

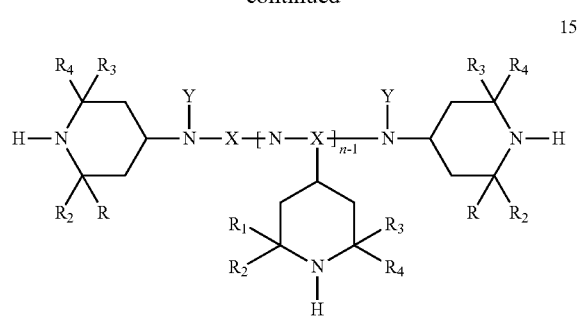

wherein $R_1, R_2, R_3$ and $R_4$ denotes a substituted or unsubstituted $C_1$ to $C_{18}$ alkylene, preferably a methyl group X denotes a difunctional substituted or unsubstituted $C_2$ to $C_{30}$ alkylene, $C_5$ to $C_{30}$ substituted or unsubstituted cycloalkylene, substituted or unsubstituted $C_5$ to $C_{30}$ arylene or heteroarylene, preferably the following structures

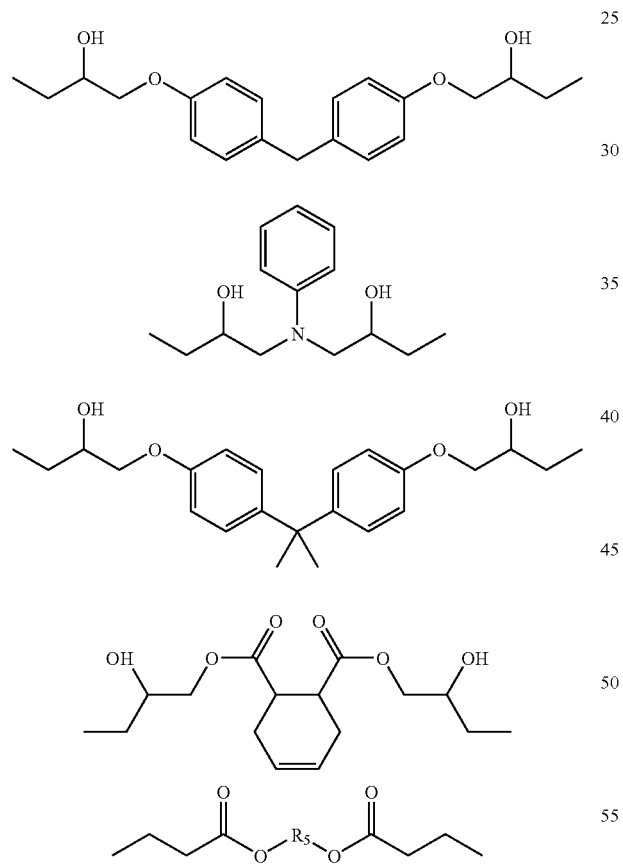

wherein $R_5$ denotes a difunctional substituted or unsubstituted $C_1$ to $C_{18}$ alkylene, $C_5$ to $C_{18}$ substituted or unsubstituted cycloalkylene, substituted or unsubstituted $C_5$ to $C_{18}$ arylene or heteroarylene, Y denotes H or a monofunctional substituted or unsubstituted $C_1$ to $C_{18}$ alkyl, $C_5$ to $C_{18}$ substituted or unsubstituted cycloalkyl, substituted or unsubstituted $C_5$ to $C_{18}$ aryl or heteroaryl, preferably selected from the group

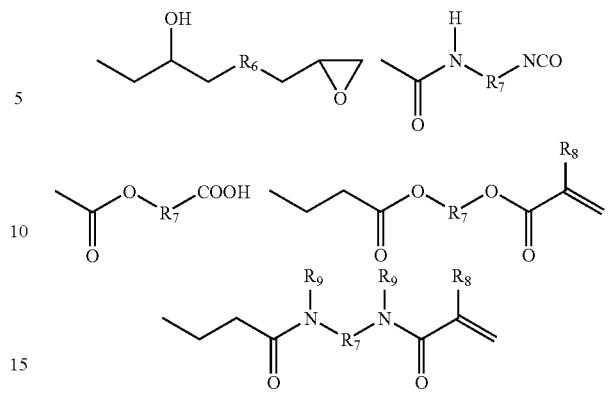

wherein $R_6$ denotes a difunctional substituted or unsubstituted $C_1$ to $C_{18}$ alkylene, $C_5$ to $C_{18}$ substituted or unsubstituted cycloalkylene, substituted or unsubstituted $C_5$ to $C_{18}$ arylene or heteroarylene, preferably

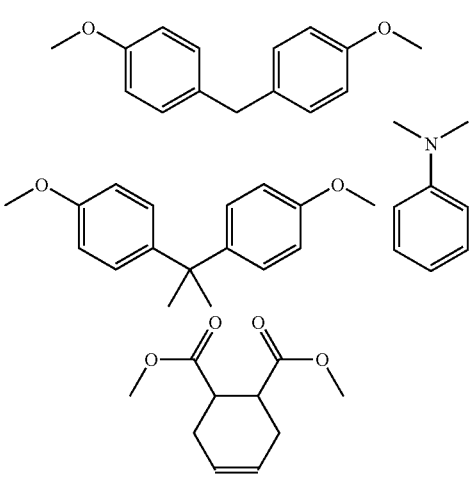

$R_7$ denotes difunctional substituted or unsubstituted $C_1$ to $C_{18}$ alkylene, $C_5$ to $C_{18}$ substituted or unsubstituted cycloalkylene, substituted or unsubstituted $C_5$ to $C_{18}$ arylene or heteroarylene, preferably selected from the group $R_8$ denotes H or a monofunctional substituted or unsubstituted $C_1$ to $C_{30}$ alkylene, $C_5$ to $C_{30}$ substituted or unsubstituted cycloalkylene, substituted or unsubstituted $C_5$ to $C_{30}$ arylene or heteroarylene $R_9$ denotes a monofunctional substituted or unsubstituted $C_1$ to $C_{30}$ alkylene, $C_5$ to $C_{30}$ substituted or unsubstituted cycloalkylene, substituted or unsubstituted $C_5$ to $C_{30}$ arylene or heteroarylene Z denotes hydrogen, or a polymerizable moiety, preferably selected from the group of

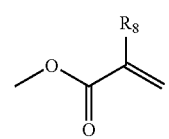

wherein
R$_8$ denotes H or a monofunctional substituted or unsubstituted C$_1$ to C$_{30}$ alkylene, C$_5$ to C$_{30}$ substituted or unsubstituted cycloalkylene, substituted or unsubstituted C$_5$ to C$_{30}$ arylene or heteroarylene
n, m and o are integers.

Furthermore, polymers, prepolymers or macromonomers comprising at least a nitroxyl radical moieties were synthesized by direct incorporation of amines 16 comprising at least a nitroxyl radical moieties

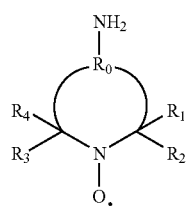

16 wherein
R$_0$ denotes a substituted or unsubstituted C$_1$ to C$_{18}$ alkylene,
R$_1$, R$_2$, R$_3$ and R$_4$ denotes a substituted or unsubstituted C$_1$ to C$_{18}$ alkylene, preferably methyl group
with a molecule of group A, selected from the group of a diepoxide, a diisocyanate, a dicarboxylic acid or a derivative thereof, a bisacrylamide or a bisacrylate or
with a molecule of group B, selected from the group of molecules that comprise at least an epoxide and a methacrylate group, an epoxide and an isocyanate, a methacrylate and an isocyanate group, an acrylate and a methacrylate group, or with a mixture of molecules A and B.

Amines containing at least a nitroxyl radical moieties are used as comonomers for synthesis of polyamides, polyamidoamines, polyesteramines, polyureas, epoxide-amine addition polymers or prepolymers or macromonomers with the corresponding structural units mentioned above.

Preferably compounds 17 and 18 were use comprising a piperidinium nitroxyl radical moiety.

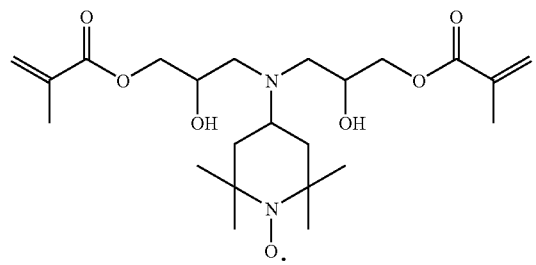

17

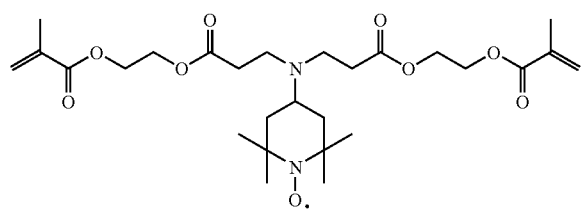

18

Surprisingly, the addition reaction of diepoxides and the steric hindered 4-amino-2,2,6,6-tetramethylpiperidin (ATMP) leads to linear soluble epoxide-amine addition polymers. The secondary amino groups do not react under the conditions of this polymerization. In the same manner the addition ATMP and Glycidylmethacrylat or Ethylene glycol acrylate methacrylate, respectively results in non-branched macromonomers.

Not less surprisingly it was found that the oxidation of prepolymers, macromonomers and polymers containing ATMP is possible without of a considerable degree of oxidation of hydroxylic moieties or methacrylic groups. The absorptions of hydroxylic groups at 3459/3421 cm$^{-1}$ and of the double bond at 1637 cm$^{-1}$ remains unchanged in the IR spectra compared to the non-oxidized molecules. Furthermore, no absorption of a keto group was observed.

The invented dental composition comprises stable radicals of formulas 1 to 5 in a content of 0.001 to 3.0% by weight, preferably in a content of 0.01 to 1.0% by weight and most preferably in a content of 0.1 to 0.5% by weight.

For example a composite containing 2,2-Bis-[p-(2-hydroxy-3-methacryloyloxypropoxy)-phenyl]-propane, Triethyleneglycol dimethacrylate, UDMA, Camphor quinone and N,N-Dimethylaminoethylbenzoic acid ethylester and a Barium-alumo-silicate glass show a light sensitivity of 25 seconds at 10,000 lux. The compressive strength is 343.9±7.3 MPa, the flexural strength (ISO 4049) is 119.2±9.3 MPa and the E-modulus is 7802±293 MPa.

A composite of the same composition that comprises additionally N,N-Bis-(2-hydroxy-3-methacryloyloxypropoxy)-4-amino-2,2,6,6-tetramethylpiperidin-1-oxyl radical of example 1 show a improved light sensitivity of 175 seconds at 10,000 lux.

EXAMPLE 1

N,N-Bis-(2-hydroxy-3-methacryloyloxypropoxy)-4-amino-2,2,6,6-tetramethylpiperidin (GMA-ATMP)

4.998 g (35.17 mmol) Glycidylmethacrylat and 2.754 g (17.59 mmol) 4-amino-2,2,6,6-tetramethylpiperidin were homogeneously mixed and reacted for 48 hours at 80° C. After that time the absorption of epoxide groups at 910 cm$^{-1}$ is completely missing.

Yield 7.756 g (100% of th.)

C$_{23}$H$_{40}$N$_2$O$_6$, 440.58 g/mol

IR (cm$^{-1}$): 3421 (OH), 2975/2935 (CH$_2$/CH$_3$), 1726 (CO), 1637 (C=C)

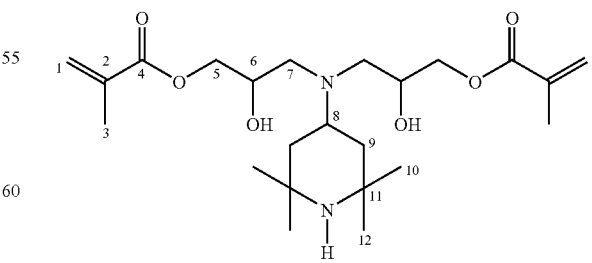

$^{13}$C NMR (ppm): 126.0 (1), 136.0 (2), 18.3 (3), 167.3 (4), 67.7/68.5 (5), 66.7/67.1 (6), 63.1 (7), 54.0/54.2 (8), 51.3/51.8 (9), 41.3 (10), 28.4/28.5 (11), 35.2 (12)

N,N-Bis-(2-hydroxy-3-methacryloyloxypropoxy)-4-amino-2,2,6,6-tetramethylpiperidin-1-oxyl radical (GMA-ATMPO)

In a three-necked flask equipped with a refluxer, a gas inlet pipe and a stirrer were dissolved 7.19 g (16.32 mmol) GMA-ATMP under stirring and heating to 60° C. Then a stream of nitrogen was passed through this solution for 30 minutes.

In 250 ml Erlenmeyer flask were dissolved under stirring 8.06 g (24.48 mmol) $K_3Fe(CN)_6$ and 4.95 g (123.65 mmol) NaOH in 180 ml water.

Thereafter the aqueous solution was added to the three-necked flask and stirred intensively for 4 hours at 23° C. The organic phase was separated and washed three times with 80 ml of deionized water and dried over $Na_2SO_4$. After removing the solvent at 50° C. and an end pressure of 3 mbar the products remains.

In the ESR spectrum a strong signal of nitroxyl radicals was found.

Yield 3.95 g (53.3% of th.)

IR (Sub.) $cm^{-1}$: $v$(O—H) 3411; $v_{as}$($CH_3$,$CH_2$) 2960, 2929; $v_s$($CH_3$,$CH_2$) 2850;

$v$(C=O) 1716; $v$(C=C) 1637; $v$(C—O) 1173

EXAMPLE 2

N,N-Bis-(2-hydroxy-3-methacryloyloxypropoxy)-4-amino-2,2,6,6-tetramethylpiperidin-1-oxyl radical (GMA-ATMPO)

1.6600 g (11.68 mmol) Glycidylmethacrylat and 1.0000 g (5.84 mmol) 4-amino-2,2,6,6-tetramethylpiperidin-1oxyl radical were homogeneously mixed and reacted 24 hours at 60° C. and 40 hours at 80° C. After that time the absorption of epoxide groups at 910 $cm^{-1}$ is completely missing.

In the ESR spectrum a strong signal of nitroxyl radicals was found.

Yield 2.660 g (100% of th.)

$C_{23}H_{39}N_2O_7$, 455.57 g/mol

IR ($cm^{-1}$): 3452 (OH), 2975/2935 ($CH_2$/$CH_3$), 1728 (CO), 1637 (C=C)

EXAMPLE 3

Poly-[3,7-dihydroxy-1,9-dioxa-5-aza-(2,2,6,6-tetramethylpiperidine) nonamethylene-1,4-phenylene isopropylidene-1,4-phenylene] (AP-ATMP)

5.0000 g (14.69 mmol) Bis-2,2-[4-(2,3-epoxypropoxy)-phenyl]-propane (DGEBA) and 2.2953 g (14.69 mmol) 4-amino-2,2,6,6-tetramethylpiperidin were slightly heated to 60° C. and mixed homogeneously. Then the mixture was reacted at 60° C. for 24 hours. After that time the absorption of epoxide groups at 915 $cm^{-1}$ is completely missing.

Yield 7.295 g (100% of th.)

$(C_{31}H_{46}N_2O_4)_n$, $(510.71)_n$ g/mol $^{13}$C NMR (ppm): 31.0 (1), 41.7 (2), 143.5 (3), 127.7 (4), 113.9 (5), 156.4 (6), 69.9 (7), 68.3/68.7 (8), 54.2/54.4 (9), 50.2 (10), 46.4 (11), 51.0/51.2 (12), 35.1/35.2 (13), 28.4/28.7 (14)

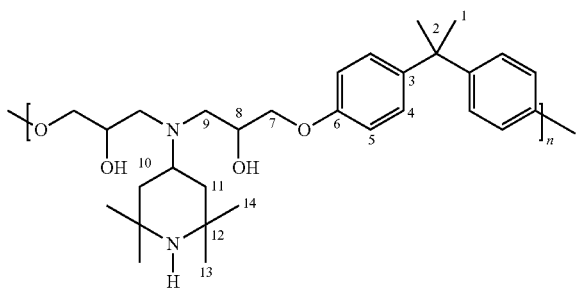

EXAMPLE 4

In a 250 ml three-necked flask equipped with a refluxer, a gas inlet pipe and a stirrer were dissolved 5.00 g (2.50 mmol) of the steric hindered amine Chimasorb 944 FD (CIBA-Geigy, CAS-Nr. 71878-19-8) in 200 ml Toluene under stirring and heating to 60° C. Then a stream of nitrogen was passed through this solution for 30 minutes.

In 250 ml Erlenmeyer flask were dissolved under stirring 10.70 g (32.50 mmol) $K_3Fe(CN)_6$ and 6.57 g (164.16 mmol) NaOH in 80 ml water.

Thereafter the aqueous solution was added to the three-necked flask and stirred intensively for 4 hours at 23° C. The organic phase was separated and washed three times with 80 ml of deionized water and dried over $Na_2SO_4$. After removing the solvent at 50° C. and an end pressure of 3 mbar the products remains.

Yield 4.33 g (86.60% of th.)

In the ESR spectrum a strong signal of nitroxyl radicals was found.

EXAMPLE 5

N,N-Bis-(3-oxa-4-oxo-6-methacryloyloxyhexyl)-4-amino-2,2,6,6-tetramethylpiperidin (AMA-ATMP)

10.000 g (63.99 mmol) 4-Amino-2,2,6,6-tetramethylpiperidin and 23.57 g (127.98 mmol) Ethylenglycol acrylatmethacrylat were homogeneously mixed and reacted at 23° C. for 14 days. After that time the absorption of acrylate double bond at 1620 $cm^{-1}$ is completely missing.

Yield 33.57 g (100% of th.)

$C_{23}H_{40}N_2O_6$, 440.58 g/mol

N,N-Bis-(3-oxa-4-oxo-6-methacryloyloxyhexyl)-4-amino-2,2,6,6-tetramethylpiperidin-1-oxyl radical (AMA-ATM PO)

N,N-Bis-(3-oxa-4-oxo-6-methacryloyloxyhexyl)-4-amino-2,2,6,6-tetramethylpiperidin was oxidized according the same procedure as described in example 1.

Yield 5.27 g (97.8% of th.)

In the ESR spectrum a strong signal of nitroxyl radicals was found.

EXAMPLE 6

N,N-Bis-(3-oxa-4-oxo-6-methacryloyloxyhexyl)-4-amino-2,2,6,6-tetramethylpiperidin-1-oxyl radical (AMA-ATMPO)

1.075 g (5.84 mmol) Ethylenglycol acrylatmethacrylat and 1.0000 g (5.84 mmol) 4-Amino-2,2,6,6-tetramethylpiperidin-1 oxyl radical were homogeneously mixed and reacted 24 hours at 60° C. and 40 hours at 80° C. After that time the absorption of acrylate double bond at 1620 cm$^{-1}$ is completely missing.

In the ESR spectrum a strong signal of nitroxyl radicals was found.

Yield 2.075 g (100% of th.)

$C_{27}H_{43}N_2O_9$, 539.65 g/mol

IR (cm$^{-1}$): 2960/2845 ($CH_2/CH_3$), 1720 (CO), 1637 (C=C)

COMPARATIVE EXAMPLE 1

39.742 g 2,2-Bis-[p-(2-hydroxy-3-methacryloyloxypropoxy)-phenyl]-propane, 24.839 g Triethyleneglycol dimethacrylate, 34.774 g Urethane dimethacrylate, 0.298 g chamfer quinone and 0.348 g Dimethylaminoethyl benzoic acid ethylester were mixed homogeneously. To this resin mixture were added 270.370 g of a barium alumo-silicate glass and mixed homogeneously.

The properties are summarized in Table 1.

APPLICATION EXAMPLE 1

39.742 g 2,2-Bis-[p-(2-hydroxy-3-methacryloyloxypropoxy)-phenyl]-propane, 24.839 g Triethyleneglycol dimethacrylate, 34.774 g Urethane dimethacrylate, 0.298 g chamfer quinone, 0.348 g Dimethylaminoethyl benzoic acid ethylester and 0.034 g 4-Amino-2,2,6,6-tetramethyl-piperidin-1-oxyl radical (Fluka) were mixed homogeneously. To this resin mixture were added 270.370 g of a barium alumo-silicate glass and mixed homogeneously.

The properties are summarized in Table 1.

APPLICATION EXAMPLE 2

39.742 g 2,2-Bis-[p-(2-hydroxy-3-methacryloyloxypropoxy)-phenyl]-propane, 24.839 g Triethyleneglycol dimethacrylate, 34.774 g Urethane dimethacrylate, 0.298 g chamfer quinone, 0.348 g Dimethylaminoethyl benzoic acid ethylester and 0.091 g GMA-ATMPO of example 2 were mixed homogeneously. To this resin mixture were added 270.370 g of a barium alumo-silicate glass and mixed homogeneously.

The properties are summarized in Table 1.

APPLICATION EXAMPLE 3

39.742 g 2,2-Bis-[p-(2-hydroxy-3-methacryloyloxypropoxy)-phenyl]-propane, 24.839 g Triethyleneglycol dimethacrylate, 34.774 g Urethane dimethacrylate, 0.298 g chamfer quinone, 0.348 g Dimethylaminoethyl benzoic acid ethylester and 0.100 g AMA-ATMPO of example 5 were mixed homogeneously. To this resin mixture were added 270.370 g of a barium alumo-silicate glass and mixed homogeneously.

The properties are summarized in Table 1.

APPLICATION EXAMPLE 4

39.742 g 2,2-Bis-[p-(2-hydroxy-3-methacryloyloxypropoxy)-phenyl]-propane, 24.839 g Triethyleneglycol dimethacrylate, 34.774 g Urethane dimethacrylate, 0.298 g chamfer quinone, 0.348 g Dimethylaminoethyl benzoic acid ethylester and 0.100 g of oxidized amine of example 4 were mixed homogeneously. To this resin mixture were added 270.370 g of a barium alumo-silicate glass and mixed homogeneously.

The properties are summarized in Table 1.

TABLE 1

Properties of dental composites of application examples 1 to 3 and of comparative example 1

| Example | | Comp. 1 | Appl. 1 | Appl. 2 | Appl. 3 |
| --- | --- | --- | --- | --- | --- |
| Sensitivity to ambient light, ISO 4049 (10000 lux) | sec | 25 | 185 | 180 | 180 |
| Compressive strength | MPa | 343.9 ± 7.3 | 318.6 ± 17.8 | 316.3 ± 11.1 | 338.5 ± 6.6 |
| Flexural strength, ISO 4049 | MPa | 119.2 ± 9.3 | 107.7 ± 10.7 | 108.3 ± 5.0 | 117.9 ± 5.6 |
| E-modulus | MPa | 7802 ± 293 | 7691 ± 343 | 7324 ± 442 | 7698 ± 212 |

We claim:

1. Dental composition having an improved light and thermal stability, comprising a mixture of
   (i) at least one polymerizable resin
   (ii) at least one polymerizable monomer
   (iii) at least one polymerization initiator and/or a sensitizer and stabilizer
   (iv) at least one organic or inorganic filler and pigments in a content of 0 to 90 percent
   (v) and at least one of the stable radicals of formulas 1, 3, 4 or 5

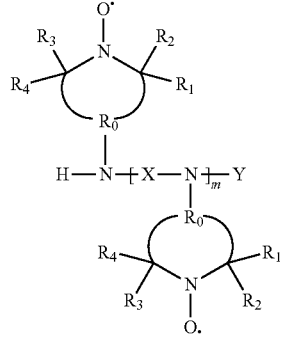

1

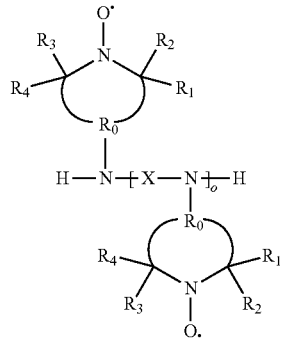

3

-continued

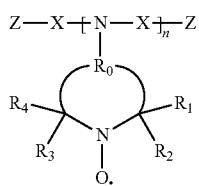

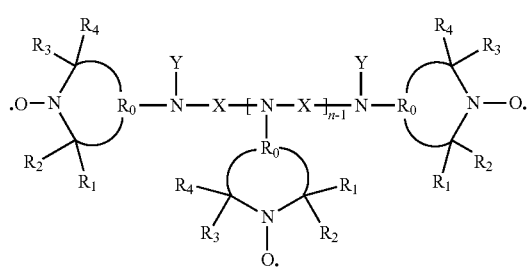

wherein
$R_0$ denotes a $C_1$ to $C_{18}$ alkylene,
$R_1$, $R_2$, $R_3$ and $R_4$ denotes a $C_1$ to $C_{18}$ alkylene,
wherein X is

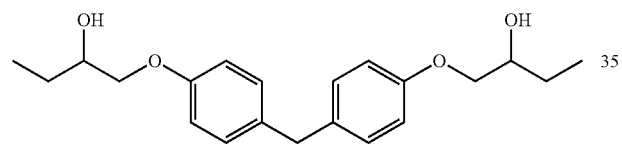

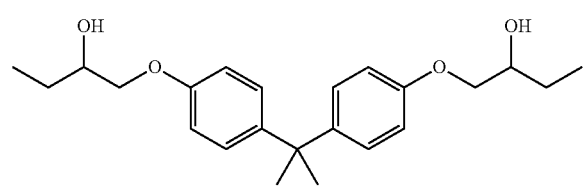

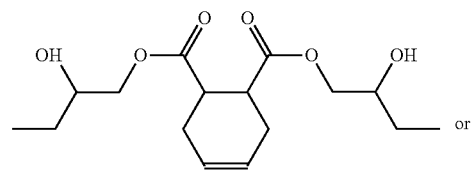

-continued

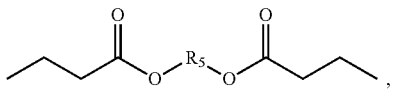

wherein Y is

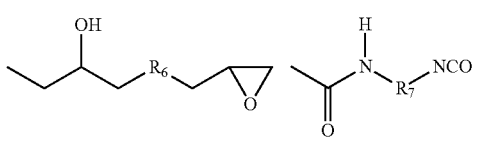

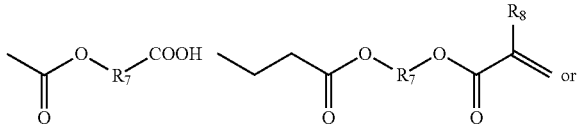

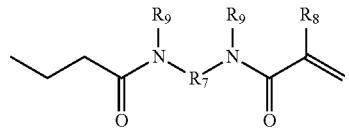

wherein Z is

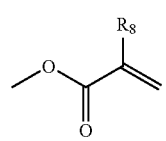

wherein
$R_5$ is a difunctional $C_1$ to $C_{18}$ alkylene, $C_5$ to $C_{18}$ cycloalkylene, or $C_5$ to $C_{18}$ arylene or heteroarylene,
$R_6$ is a difunctional $C_1$ to $C_{18}$ alkylene, $C_5$ to $C_{18}$ cycloalkylene, or $C_5$ to $C_{18}$ arylene or heteroarylene,
$R_7$ is difunctional $C_1$ to $C_{18}$ alkylene, $C_5$ to $C_{18}$ cycloalkylene, or $C_5$ to $C_{18}$ arylene or heteroarylene,
$R_8$ is H, a monofunctional $C_2$ to $C_{30}$ alkylene, $C_5$ to $C_{30}$ cycloalkylene, or $C_5$ to $C_{30}$ arylene or heteroarylene, and
$R_9$ is a monofunctional $C_2$ to $C_{30}$ alkylene, $C_5$ to $C_{30}$ cycloalkylene, or $C_5$ to $C_{30}$ arylene or heteroarylene,
wherein
n, m and o are positive integers.

2. Dental composition of claim 1, comprising at least one of the compounds 6, 8, 9 or 10 having at least one piperidinium nitroxyl radical moiety

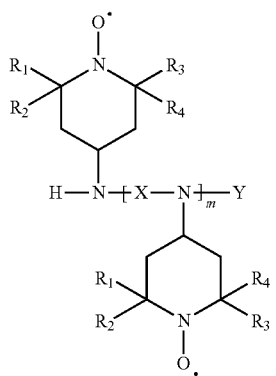
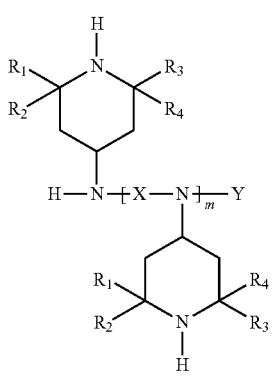
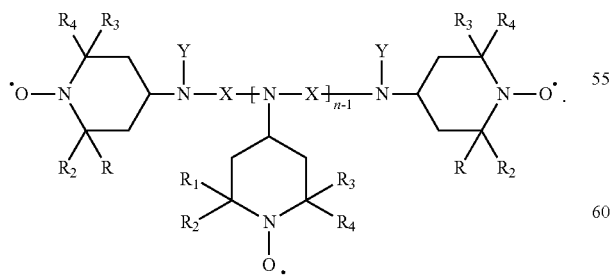
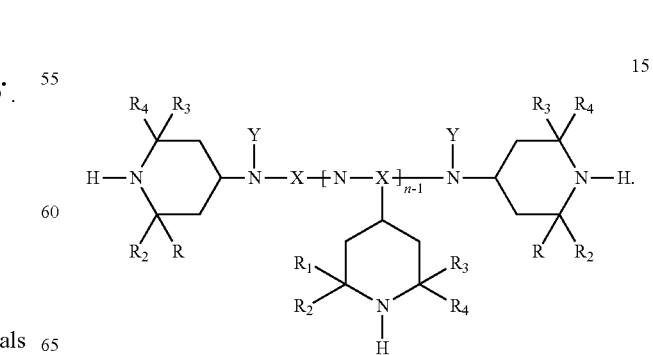
3. Dental composition of claim 1, wherein stable radicals of formulas 1, 3, 4 or 5 are obtained by oxidation of one of the compounds 11, 13, 14 or 15

4. Dental composition of claim 1, wherein the stable radicals of formulas 1, 3, 4 or 5 were obtained by reaction of compound 16

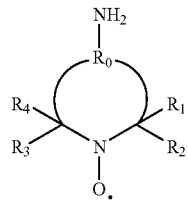

16 with a molecule A selected from the group consisting of a diepoxide, a diisocyanate, a dicarboxylic acid, a bisacrylamide, and a bisacrylate;
with a molecule B selected from the group consisting of molecules that include at least an epoxide and a methacrylate group, molecules that include at least an epoxide and an isocyanate, molecules that include at least a methacrylate and an isocyanate group, and molecules that include at least an acrylate and a methacrylate group, or
with a mixture of molecules A and B
wherein
$R_0$ is a $C_1$ to $C_{18}$ alkylene, and
$R_1$, $R_2$, $R_3$ and $R_4$ denote a $C_1$ to $C_{18}$ alkylene.

5. Dental composition of claim 4, wherein the stable radicals are present as comonomers in polyamides, polyamidoamines, polyesteramines, polyureas, or epoxide-amine polymers.

6. Dental composition of claim 4, wherein the stable radicals are present as comonomers in macromonomers or prepolymers having polyamide, polyamidoamine, polyesteramine, polyurea or epoxide-amine polymer structural units.

7. Dental composition of claim 1, wherein the stable radicals are compound 17 or 18

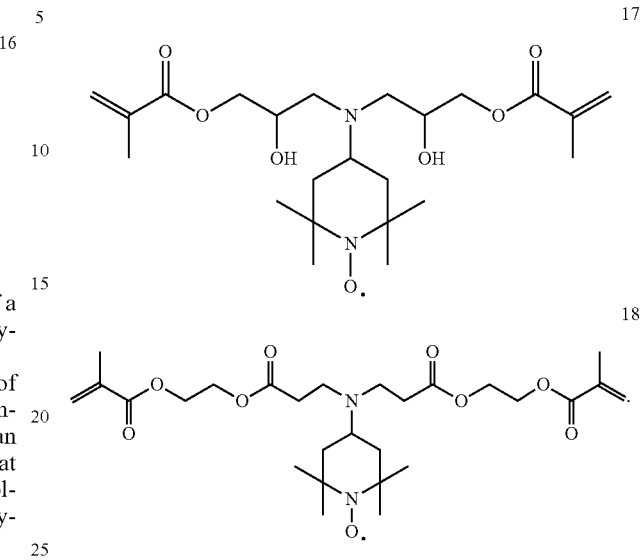

8. Dental composition of claim 1, wherein the dental composition comprises stable radicals of formulas 1, 3, 4 or 5 in a content of 0.001 to 3.0% by weight.

9. Dental composition of claim 1, wherein the dental composition comprises stable radicals of formulas 1, 3, 4 or 5 in a content of 0.01 to 1.0% by weight.

10. Dental composition of claim 1, wherein the dental composition most comprises stable radicals of formulas 1, 3, 4 or 5 in a content of 0.01 to 0.2% by weight.

* * * * *